United States Patent
Nakano et al.

(10) Patent No.: US 11,935,233 B2
(45) Date of Patent: *Mar. 19, 2024

(54) NEURAL NETWORK CLASSIFICATION

(71) Applicant: INTERNATIONAL BUSINESS MACHINES CORPORATION, Armonk, NY (US)

(72) Inventors: Hiroki Nakano, Otsu (JP); Masaharu Sakamoto, Yokohama (JP)

(73) Assignee: International Business Machines Corporation, Armonk, NY (US)

(*) Notice: Subject to any disclaimer, the term of this patent is extended or adjusted under 35 U.S.C. 154(b) by 155 days.

This patent is subject to a terminal disclaimer.

(21) Appl. No.: 17/444,756

(22) Filed: Aug. 10, 2021

(65) Prior Publication Data

US 2021/0374958 A1   Dec. 2, 2021

Related U.S. Application Data

(63) Continuation of application No. 15/802,944, filed on Nov. 3, 2017, now Pat. No. 11,138,724, which is a
(Continued)

(51) Int. Cl.
*G01N 33/48* (2006.01)
*G01N 33/50* (2006.01)
(Continued)

(52) U.S. Cl.
CPC .......... *G06T 7/0012* (2013.01); *G06F 18/217* (2023.01); *G06F 18/2185* (2023.01);
(Continued)

(58) Field of Classification Search
CPC ....... G06T 7/0012; G06T 1/20; G06F 18/217; G06F 2218/12; G06N 3/08
See application file for complete search history.

(56) References Cited

U.S. PATENT DOCUMENTS

| 8,126,267 B2 | 2/2012 | Talati et al. |
| 8,811,697 B2 | 8/2014 | Sofka et al. |
| (Continued) | | |

FOREIGN PATENT DOCUMENTS

| CN | 103824049 A | 5/2014 |
| CN | 105631519 A | 6/2016 |
| (Continued) | | |

OTHER PUBLICATIONS

English machine translation of CN 103824049 A. (Year: 2023).*
(Continued)

*Primary Examiner* — Russell S Negin
(74) *Attorney, Agent, or Firm* — Michael O'Keefe

(57) ABSTRACT

Neural network classification may be performed by inputting a training data set into each of a plurality of first neural networks, the training data set including a plurality of samples, obtaining a plurality of output value sets from the plurality of first neural networks, each output value set including a plurality of output values corresponding to one of the plurality of samples, each output value being output from a corresponding first neural network in response to the inputting of one of the samples of the training data set, inputting the plurality of output value sets into a second neural network, and training the second neural network to output an expected result corresponding to each sample in response to the inputting of a corresponding output value set.

13 Claims, 8 Drawing Sheets

Related U.S. Application Data continuation of application No. 15/611,065, filed on Jun. 1, 2017, now Pat. No. 10,713,783.

(51) Int. Cl.

| | |
|---|---|
| *G06F 18/21* | (2023.01) |
| *G06F 18/2413* | (2023.01) |
| *G06F 18/243* | (2023.01) |
| *G06N 3/045* | (2023.01) |
| *G06N 3/08* | (2023.01) |
| *G06T 1/20* | (2006.01) |
| *G06T 7/00* | (2017.01) |
| *G06V 10/764* | (2022.01) |
| *G06V 10/778* | (2022.01) |
| *G06V 10/82* | (2022.01) |
| *G16H 30/40* | (2018.01) |
| *G16H 50/20* | (2018.01) |

(52) U.S. Cl.
CPC .. *G06F 18/24143* (2023.01); *G06F 18/24317* (2023.01); *G06N 3/045* (2023.01); *G06N 3/08* (2013.01); *G06T 1/20* (2013.01); *G06V 10/764* (2022.01); *G06V 10/7788* (2022.01); *G06V 10/82* (2022.01); *G16H 30/40* (2018.01); *G16H 50/20* (2018.01); *G06F 2218/12* (2023.01); *G06T 2207/30061* (2013.01)

(56) References Cited

U.S. PATENT DOCUMENTS

| | | | |
|---|---|---|---|
| 10,599,977 | B2 | 3/2020 | Nakano |
| 10,713,783 | B2 | 7/2020 | Nakano |
| 11,138,724 | B2 * | 10/2021 | Nakano .............. G06T 1/20 |
| 2008/0187241 | A1 | 8/2008 | Talati |
| 2010/0266185 | A1 | 10/2010 | Matulewicz |
| 2015/0095017 | A1 | 4/2015 | Mnih |
| 2015/0213302 | A1 | 7/2015 | Madabhushi et al. |
| 2016/0026851 | A1 | 1/2016 | Divekar et al. |
| 2016/0157831 | A1 | 6/2016 | Kang et al. |
| 2016/0180162 | A1 | 6/2016 | Cetintas |
| 2018/0060723 | A1 | 3/2018 | Nakano |
| 2018/0350065 | A1 | 12/2018 | Nakano |
| 2018/0350069 | A1 | 12/2018 | Nakano |
| 2019/0012768 | A1 | 1/2019 | Tafazoli Bilandi |

FOREIGN PATENT DOCUMENTS

| | | |
|---|---|---|
| CN | 106056210 A | 10/2016 |
| CN | 110622175 A | 12/2019 |
| DE | 112018002822 T5 | 2/2020 |
| GB | 2577017 A | 1/2020 |
| JP | 10171910 A | 6/1998 |
| JP | 2014049118 A | 3/2014 |
| JP | 2020522794 A | 7/2020 |
| WO | 2014075017 A1 | 5/2014 |
| WO | 2018220566 A1 | 12/2018 |

OTHER PUBLICATIONS

Havaei et al. Brain tumor segmentation with deep neural networks. arXiv:1505.03540v3, May 20, 2016, 17 pages.*
IBM: List of IBM Patents or Patent Applications Treated as Related (Appendix P), Sep. 10, 2021, pp. 1-2.
Chen et al., "Hippocampus Segmentation Through Multi-View Ensemble Convnets", 2017 IEEE 14th International Symposium on Biomedical Imaging (ISBI 2017), , IEEE, 2017, 7 pages.
Sakamoto et al., "Multi-stage Neural Networks with Single-sided Classifiers for False Positive Reduction and its Evaluation using Lung X-ray CT Images," arXiv: 1703.00311v3 [cs.CV] Mar. 21, 2017, https://arxiv.org/pdf/1703.00311v3.pdf, 11 pages.
"LROC&FROC", retrieved from http://www.clg.niigatau.ac.jp/~medimg/practice_medical_imaging/roc/3lfroc/index.htm on Jun. 28, 2016.
"Synapse (PACS)", retrieved from http://www.fujifilm.com/products/medical/synapse/ on Jun. 28, 2016.
Cancer Research UK, http://www.cancerresearchuk.org/health-professional/cancer-statistics/statistics-by-cancer-type/lung\cancer/mortality, retrieved Jun. 24, 2016.
Devinder Kumar, et al., "Discovery Radiomics for Computed Tomography Cancer Detection", arXiv:1509.00117 [cs.CV], Sep. 2015. {Retrieved from https://arxiv.org/abs/1509.00117].
International Search Report and Written Opinion of International Application No. PCT/IB2018/053870, dated Sep. 29, 2018, 14 pages.
Setio, A.A.A. et al., "Pulmonary Nodule Detection in CT Images: False Positive Reduction Using Multi-View Convolutional Networks," IEEE Trans. on Medical Imaging, vol. 35, No. 5 (May 2016).
V.P. Gladis Pushap Rathi, et. al., "Brain Tumor Detection and Classification Using Deep Learning Classifier on MRI Images", Research Journal of Applie dSciences, Engineering and Technology 10(2), pp. 177-187, May 2015.
Mohammad Havaei, et. al., Brain Tumor Segmentation with Deep Neural Networks, arXiv:1505.03540 [cs.CV], May 2015. [Retrieved from https://arxiv.org/abs/1505.03540].
Quin et al. "Joint Training of Cascaded CNN for Face Detection". IEEE CVPR, Jun. 2016, pp. 3456-3465.
Examination Report of European Application No. GB1917993.6, dated Jan. 28, 2022, 5 pages.
UK Examination Report of European Application No. GB1917993.6, dated May 20, 2022, 5 pages.

* cited by examiner

NEURAL NETWORK CLASSIFICATION

BACKGROUND

Technical Field

The present invention relates to neural network classification and training thereof. More specifically, the present invention relates to training of a neural network based on compositions of output from a plurality of first neural networks for classification.

Related Art

Lung cancer occupies a high percentage among mortality rates of cancer victims even on a worldwide basis. Early detection is one of the most promising strategies to reduce lung cancer mortality. In recent years, along with performance improvements of Computed Tomography (CT) equipment, increasingly large numbers of tomographic images have come to be taken (e.g., at slice intervals of 1 mm), resulting in improvements in the ability of radiologists to distinguish nodules. However, there is a limitation in the human ability to competently interpret a large number of images, which could be around 300-500 slices per scan. Computer-aided diagnosis (CAD) systems show promise for the urgent task of time-efficient interpretation of CT scans, but these systems can issue false positives, which can be a problem. Some current methods use cascaded neural networks with selective classifiers for lung nodule detection in CT scan images.

One such current method is known as ensemble learning. In ensemble learning, the first step involves creating multiple neural networks, known as models, and then aggregating the generated models through techniques such as voting or averaging. Models may be identified as weak if it produces a substantial error rate, but the performance is not random. Boosting incrementally builds an ensemble by training each model with the same dataset, but where the weights of instances are adjusted according to the error of the last prediction. A combination of simpler learners may be used to improve predictions. Different input regions may be cover different learners.

Another such current method involves the use of multi-view convolutional networks. For example, multiple 2D images of different planes may extracted from a 3D volume generated through computed tomography. Each of the Convolutional Neural Networks (CNN) stream processes one of the 2D images extracted from a specific view. The output of all of the CNNs are fused, and a nodule probability is computed.

These current methods of using cascaded neural networks with selective classifiers can reduce the false positives of lung nodule detection in CT scan images. However, there is room for performance improvements using the models.

SUMMARY

According to a first aspect of the present invention, provided is a method including inputting a training data set into each of a plurality of first neural networks, the training data set including a plurality of samples, obtaining a plurality of output value sets from the plurality of first neural networks, each output value set including a plurality of output values corresponding to one of the plurality of samples, each output value being output from a corresponding first neural network in response to the inputting of one of the samples of the training data set, inputting the plurality of output value sets into a second neural network, and training the second neural network to output an expected result corresponding to each sample in response to the inputting of a corresponding output value set. According to the first aspect, the method may improve the reduction of false positives in applicable situations. The first aspect may also include a program for implementing the method, a processor executing the program, and an apparatus that performs the method.

According to a second aspect of the present invention, provided is the method of the first aspect, further including deriving the plurality of first neural networks from a cascaded Convolutional Neural Network (CNN). According to the second aspect, the method may improve the discrimination ability by cascading classifiers, and in doing so train a final stage neural network based on the previous stage's discrimination results.

According to a third aspect of the present invention, provided is the method of the first aspect, further including training each first neural network of the plurality of first neural networks to output the expected result corresponding to each sample in response to the inputting of the corresponding sample, through multi-fold cross validation of a multi-stage CNN. According to the third aspect, the plurality of first neural networks may have a more balanced ability to correctly output the expected result.

According to a fourth aspect of the present invention, provided is the method of the first aspect, wherein each sample includes a plurality of aspects, and each aspect corresponds to one of the plurality of first neural networks, and each first neural network among the plurality of first neural networks is trained by inputting the corresponding aspect among the plurality of aspects. According to the fourth aspect, each first neural network may become sensitive to the subtleties of its respective aspect, which may influence the results, improving the reduction of false positives in applicable situations.

According to a fifth aspect of the present invention, provided is the method of the first aspect, further including recording the second neural network as a second weight value set, the second weight value set being the result of the training of the second neural network. According to the fifth aspect, the resultant composition of neural networks may be distributed in its already trained form, ready to be used for classification. The fifth aspect may also include a computer program product including a computer-readable medium storing the plurality of first neural networks, each first neural network stored as a first weight value set, and the second neural network as the second weight value set.

According to a sixth aspect of the present invention, provided is the method of the first aspect, further including training a plurality of second neural networks to output an expected result corresponding to each sample in response to the inputting of a corresponding output value set, each second neural network input with output value sets from a corresponding plurality of first neural networks, and training a third neural network to output an expected result corresponding to each sample in response to the inputting of output corresponding to the sample from the plurality of second neural networks. According to the sixth aspect, an additional layer of the composition may improve the reduction in false positives in applicable situations.

According to a seventh aspect of the present invention, provided is a method including inputting a sample into each of a plurality of first neural networks, obtaining an output value set from the plurality of first neural networks, the output value set including a plurality of output values corresponding to the sample, each output value being output from a corresponding first neural network in response to the inputting of the sample, inputting the output value set into a second neural network, obtaining a result corresponding to the sample in response to the inputting of a the output value set, and outputting the result. According to the seventh aspect, the trained first and second neural networks may be used to determine an unknown result, such as a classification, such as whether or not a sample includes a nodule.

The summary clause does not necessarily describe all necessary features of the embodiments of the present invention. The present invention may also be a sub-combination of the features described above.

DESCRIPTION OF EXEMPLARY EMBODIMENTS

Hereinafter, example embodiments of the present invention will be described. The example embodiments shall not limit the invention according to the claims, and the combinations of the features described in the embodiments are not necessarily essential to the invention.

Embodiments of the present invention may include cascaded neural networks including CNNs that perform as selective classifiers for filtering out obvious non-nodules, such as blood vessels or ribs, followed by a CNN trained with a balanced data set for calculating nodule probabilities.

In some embodiments, cascaded CNNs includes $S_1$-$S_n$ may perform as selective classifiers to filter out non-nodule lesions. A further cascaded CNN, $S_{n+1}$, may obtain nodule probabilities. As such, n*N models may be derived through N-fold cross validation. For example, fifty models may be derived from 5-stage cascaded CNNs ($S_1$-$S_5$) with 10-fold cross validation. By inputting a nodule candidate image, or images extracted from a 3D image volume, to the derived models, a nodule probability vector of length equal to n*N can be obtained. Another neural network model may be trained by using the nodule probability vectors obtained from the derived models. This neural network model may provide superior performance by learning the pattern(s) of nodule probabilities generated from the derived models.

Figure 1:
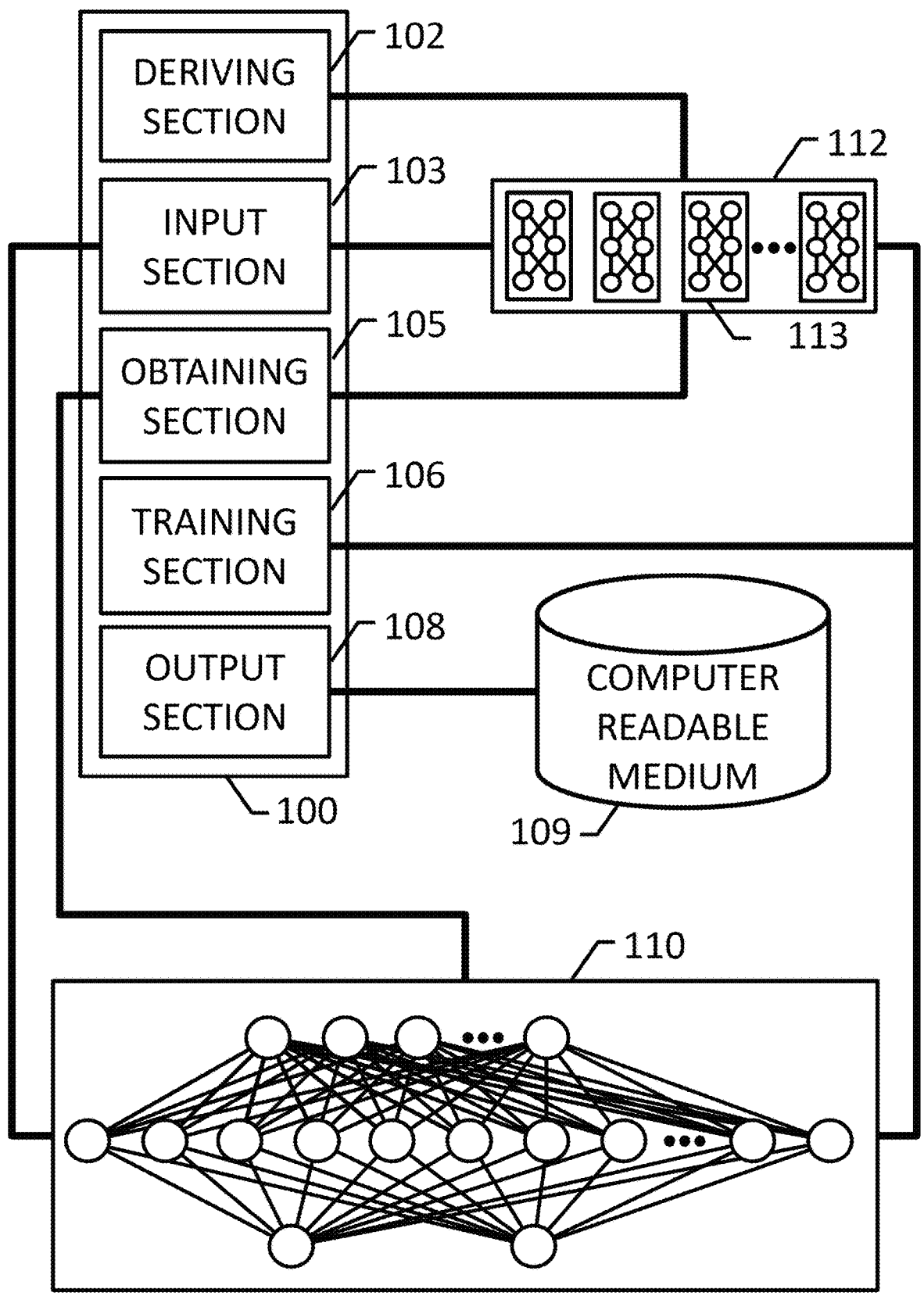
FIG. 1 shows an apparatus for neural network classification and training thereof, according to an embodiment of the present invention.

FIG. 1 shows an apparatus 100 for neural network classification and training thereof, according to an embodiment of the present invention. Apparatus 100 may be a host computer such as a server computer or a mainframe computer that executes an on-premise application and hosts client computers that use it. Apparatus 100 may be a computer system that includes two or more computers. Alternatively, apparatus 100 may be a personal computer that executes an application for a user of apparatus 100.

Apparatus 100 may include a deriving section 102, an input section 103, an obtaining section 105, a training section 106, and an output section 108. Apparatus 100 may be in communication with a computer-readable medium 109, a second neural network 110, and a plurality of first neural networks 112. Apparatus 100 may be a computer program product including one or more computer readable storage mediums collectively storing program instructions that are executable by a processor to cause the processor to perform the operations of the various sections. Apparatus 100 may alternatively be analog or digital programmable circuitry, or any combination thereof. Apparatus 100 may be composed of physically separated storage or circuitry that interacts through communication.

Each first neural network 113 of plurality of first neural networks 112 may be a neural network configured to output a probability of a classification of a raw sample, or any other input. Second neural network 110 may be a neural network configured to output a value relating to the classification of input, such as a probability of a classification, based on a composition of output probabilities of the classification. These neural networks may be stored locally or remotely. First neural networks 112 and second neural network 110 may be any type of neural network including but not limited to feed-forward neural networks, recurrent neural networks, modular neural networks, dynamic neural networks, cascading neural networks, etc., in any combination. In some embodiments, first neural networks 112 and second neural network 110 may be realized by software programs executed in apparatus 100, while in other embodiments first neural networks 112 and second neural network 110 may be realized by a computer or computers in communication with apparatus 100, realized as physical neural networks, etc.

Deriving section 102 may derive neural networks configured to output a probability of a classification of a raw sample, such as first neural network 113. In some embodiments, deriving section 102 may be configured to derive plurality of first neural networks 112 from a cascaded Convolutional Neural Network (CNN). In other embodiments, deriving section 102 may be configured to derive plurality of first neural networks 112 by adjusting a hyper-parameter of an initial first neural network to create an ensemble. Such adjustment may be random or determined based on results, such as results during training.

Input section 103 may input samples, probabilities, or other forms of data into neural networks, such as first neural network 113 and second neural network 110. In some embodiments, input section 103 may be configured to input a training data set into each of plurality of first neural networks 112, the training data set including a plurality of samples, and also configured to input a plurality of output value sets into second neural network 110. Input section 103 may be in communication with a memory, a computer, a server, etc., from which to receive samples, probabilities, and other forms of data. Examples of a sample may include a 3D image volume, a 2D image, a collection of diagnostics, etc. Input section 103 may receive probabilities from obtaining section 105.

Obtaining section 105 may obtain output from neural networks, such as first neural network 113 and second neural network 110. In some embodiments, obtaining section 105 may be configured to obtain the plurality of output value sets from plurality of first neural networks 112, each output value set including a plurality of output values corresponding to one of the plurality of samples, each output value being output from a corresponding first neural network in response to the inputting of one of the samples of the training data set. Obtaining section 105 may send output values from plurality of first neural networks 112 to input section 103 so that the output values may be input as output value sets into second neural network 110.

Training section 106 may train neural networks, such as first neural network 113 and second neural network 110. In some embodiments, training section 106 may be configured to train each first neural network of the plurality of first neural networks. Such training may include adjustment of parameters in order to improve the ability of the neural network to correctly output an expected result. In some embodiments, training section 106 may be configured to train the second neural network to output an expected result corresponding to each sample in response to the inputting of a corresponding output value set. In these and other embodiments, training section 106 may be further configured to train each first neural network to output the expected result corresponding to each sample in response to the inputting of the corresponding sample. The training by training section 106 may include adjustment of hyper-parameters or other and more complex forms of training, including derivation of neural networks within the process of training. In some embodiments, training section 106 is further configured to multi-fold cross validate a multi-stage CNN. Training section 106 may operate in cooperation with deriving section 102 during training.

Output section 108 may output probabilities and results obtained by the obtaining section 105 or may record neural networks as weight value sets. In some embodiments, output section 108 may be configured to record the second neural network as a second weight value set, the second weight value set being the result of the training of the second neural network. In other embodiments, output section 108 may be configured to output a result of the second neural network.

Computer-readable medium 109 may store data for use by apparatus 100 or the individual sections. In some embodiments, computer-readable medium 109 may store the plurality of first neural networks and the second neural network, each first neural network stored as a first weight value set, and the second neural network stored as the second weight value set. In other embodiments, computer-readable medium 109 may store samples, output values, results, and any other data that may be useful to apparatus 100. Computer-readable medium 109 may be in direct or indirect communication with the sections of apparatus 100, such as through a server across a network.

Figure 2A:
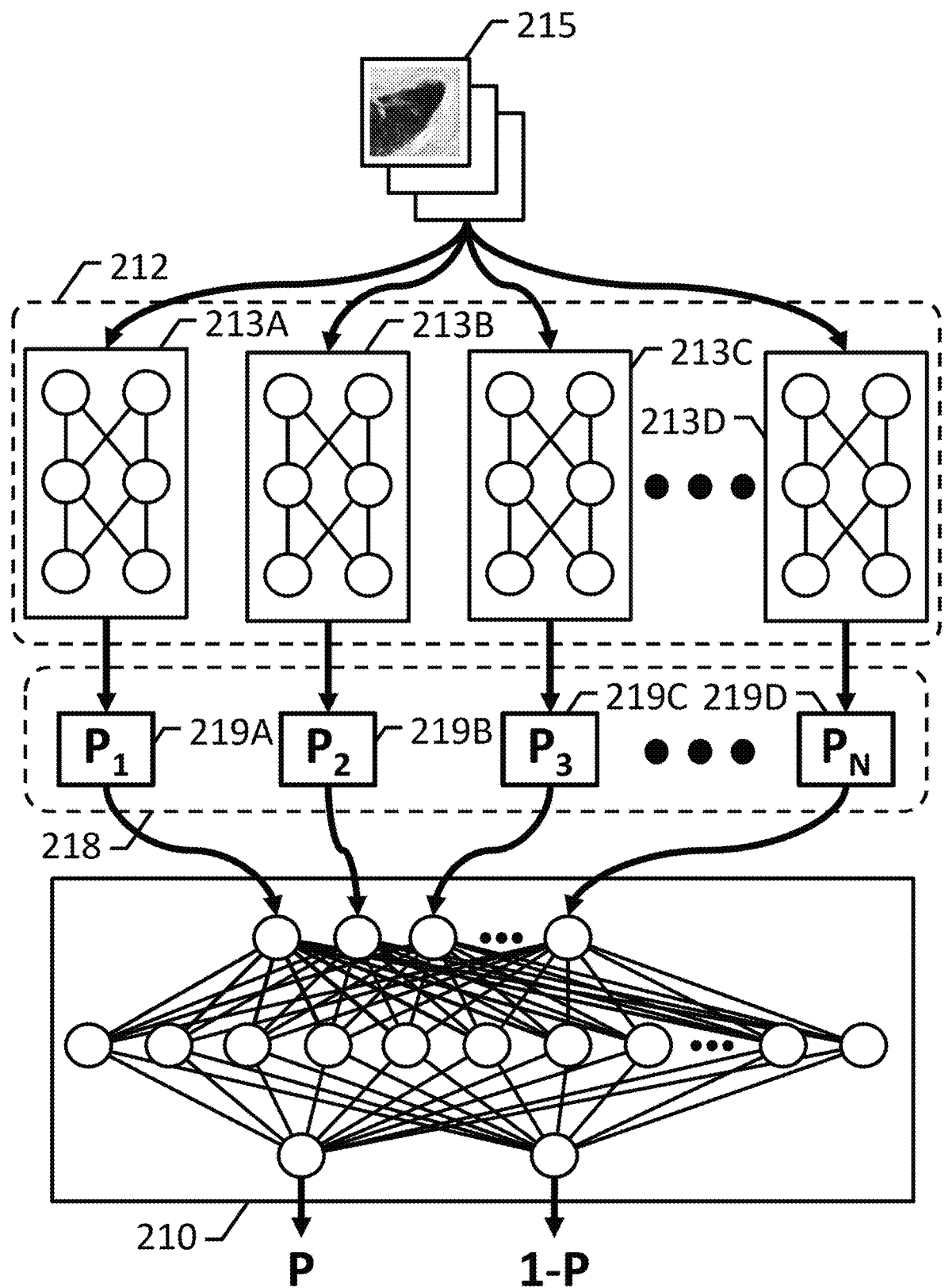
FIG. 2A shows a composition of the first neural networks and the second neural network, according to an embodiment of the present invention.

FIG. 2A shows a composition of the first neural networks and the second neural network, according to an embodiment of the present invention. The composition includes a plurality of first neural networks 212, including at least first neural networks 213A, 213B, 213C, and 213D, and second neural network 210. In particular, FIG. 2 shows a flow of data as sample 215 is input into a plurality of first neural networks 212, output 218 of first neural networks 212 is input into second neural network 210, and an output of second neural network 210 is obtained therefrom.

In this embodiment, each first neural network (213A-213D) may receive the same input, sample 215. In these and other embodiments, the training of each first neural network among the plurality of first neural networks includes inputting each sample among the plurality of samples.

The number of input nodes each first neural network (213A-213D) may be configured to match the amount of data from sample 215, and thus is uniform among the plurality of first neural networks 212 in this embodiment. In some embodiments, each first neural network (213A-213D) among plurality of first neural networks 212 may have a first network structure. In other embodiments, at least one first neural network among plurality of first neural networks 212 may have a first network structure, and at least one first neural network among plurality of first neural networks 212 may have a second network structure. The number of output nodes of each first neural network (213A-213D) may be one, such as for a single probability of the sample falling into a certain classification.

The number of input nodes of second neural network 210 may match the number of first neural networks among plurality of neural networks 212. In this manner, each output (219A-219D) may be input into a unique node of second neural network 210. In many embodiments, input nodes of second neural network 210 consistently receive output from the same first neural network. In this manner, second neural network 210 may learn habits of each first neural network (213A-213D), which may influence the results, improving the reduction of false positives in applicable situations. Second neural network may have two output nodes, such as one for a probability that the sample will fall into a certain classification, and another output node for the probability that it will not, which is usually one minus the probability from the one node.

Figure 2B:
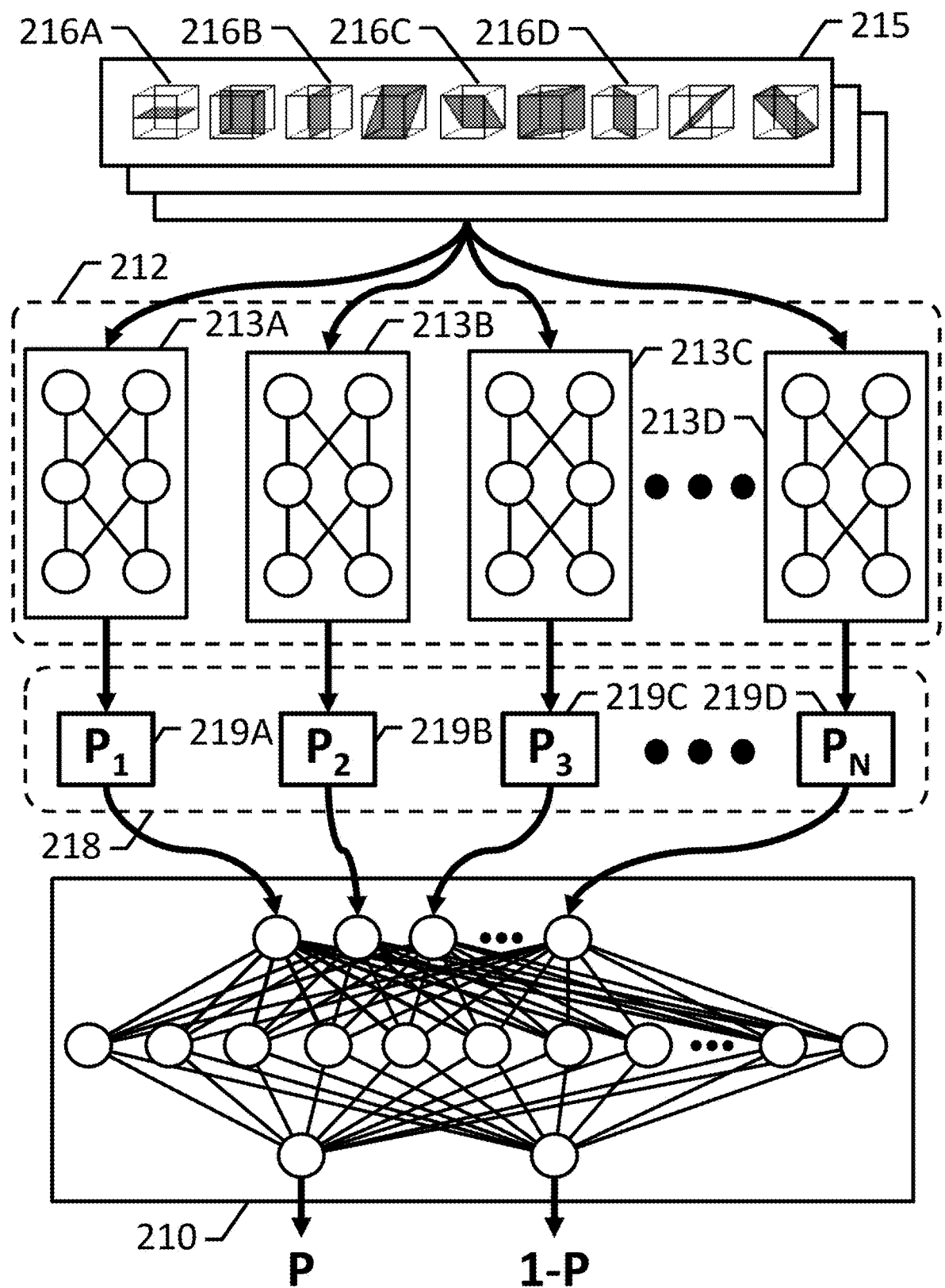
FIG. 2B shows a composition of the first neural networks and the second neural network, according to an embodiment of the present invention.

FIG. 2B shows a composition of the first neural networks and the second neural network, according to an embodiment of the present invention. The composition includes a plurality of first neural networks 212, including at least first neural networks 213A, 213B, 213C, and 213D, and second neural network 210. In particular, FIG. 2 shows a flow of data as sample 215 is input into a plurality of first neural networks 212, output 218 of first neural networks 212 is input into second neural network 210, and an output of second neural network 210 is obtained therefrom.

Sample 215 may include multiple aspects, such as aspect 216A, aspect 216B, aspect 216C, and aspect 216D, which may be extracted or otherwise obtained from sample 215. In some embodiments, sample 215 may include a plurality of aspects, and each aspect corresponds to one of plurality of first neural networks 212. In these and other embodiments, the training of each first neural network (213A-213D) among plurality of first neural networks 212 may include inputting the corresponding aspect among the plurality of aspects (216A-216D). For example, aspect 216A is input into first neural network 213A. In some embodiments, the sample may be a 3D image, and each aspect is an image of a plane within the 3D image. In these and other embodiments, each first neural network (213A-213D) may be configured or trained to receive a certain type of aspect, such as images of a certain plane from 3D image volumes. In this manner, each first neural network (213A-213D) may become sensitive to the subtleties of its respective aspect, which may influence the results, improving the reduction of false positives in applicable situations. In other embodiments, the sample may be an organism, and each aspect is a diagnostic of the organism.

The number of input nodes each first neural network (213A-213D) may be configured to match the amount of data from each aspect (216A-216D). This amount may be uniform among plurality of first neural networks 212, which may be appropriate in embodiments where each aspect is an image of a plane within the 3D image. However, this amount may also differ among plurality of first neural networks 212, which may be appropriate where each aspect is a diagnostic of an organism. In broader terms, in some embodiments, each first neural network (213A-213D) among plurality of first neural networks 212 may in broader terms have a first network structure. In other embodiments, at least one first neural network among plurality of first neural networks 212 may have a first network structure, and at least one first neural network among plurality of first neural networks 212 may have a second network structure. The number of output nodes of each first neural network (213A-213D) may be one, such as for a single probability of the sample falling into a certain classification.

Figure 3:
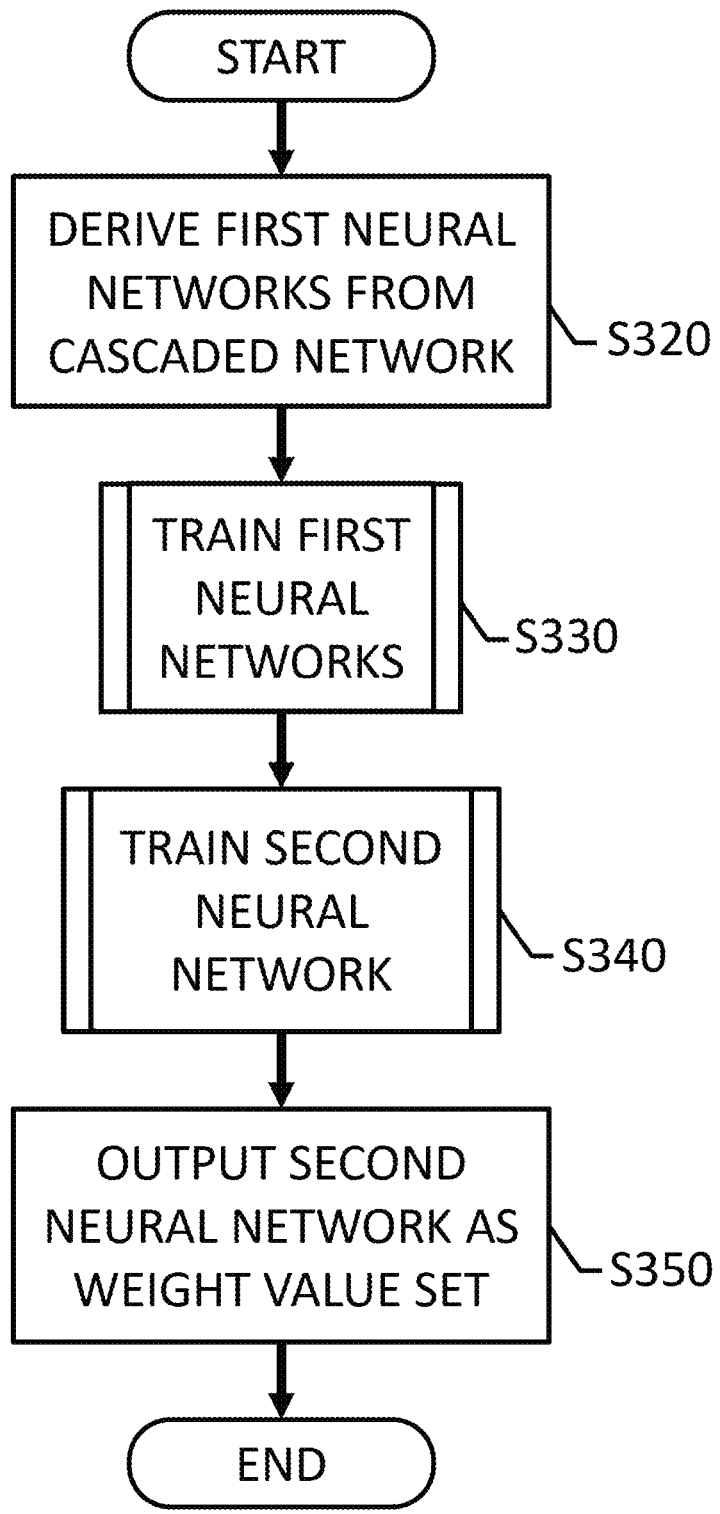
FIG. 3 shows an operational flow for neural network classification and training thereof, according to an embodiment of the present invention.

FIG. 3 shows an operational flow for neural network classification and training thereof, according to an embodiment of the present invention. The operational flow may provide a method of neural network classification and training thereof, such as that of the composition of plurality of first neural networks 212 and second neural network 210. The operations may be performed by an apparatus, such as apparatus 100.

At S320, a deriving section, such as deriving section 102, may derive a plurality of first neural networks, such as plurality of first neural networks 212, from a cascaded network. In some embodiments, this may include deriving the plurality of first neural networks from a cascaded Convolutional Neural Network (CNN). For example, the deriving section may begin with 10 5-stage cascaded neural networks. In this example, deriving section may then yield 50 first neural networks.

At S330, a training section, such as training section 106, may train each first neural network of the plurality of first neural networks. In some embodiments, this may include training each first neural network to output the expected result corresponding to each sample in response to the inputting of the corresponding sample. In embodiments in which the first neural networks are derived from a cascaded CNN, the training of each first neural network among the plurality of first neural networks may include multi-fold cross validating a multi-stage CNN. In such embodiments, output in the form of probability vectors may be obtained with each stage of the cascaded CNN, wherein the first neural networks, or cascaded classifiers, may be created or derived using neural networks while improving discrimination ability by cascading the classifiers and in doing so training the (n+1)-th stage neural network based on n-th stage discrimination results. In some embodiments, the training section trains the first neural networks as part of the deriving process, in which each of the 10 neural networks are trained with a different set of training data.

At S340, the training section may train the second neural network. In some embodiments, the training section may train the second neural network to output an expected result corresponding to each sample in response to the inputting of a corresponding output value set.

At S350, an output section, such as output section 108, may record the second neural network as a second weight value set. In some embodiments, the second weight value set may be the result of the training (S340) of the second neural network. In these and other embodiments, the first neural networks may also be recorded as first weight value sets. For example, the first and second weight value sets may be recorded to a computer-readable medium. The computer-readable medium may then be distributed to those who may benefit from a neural network trained for classification, such as classification of 3D image volumes based on whether or not a nodule is present. In some embodiments, the output section may also record information concerning the structure of the first and second neural networks.

In alternate embodiments, the operational flow may also involve the training of a plurality of second neural networks. In such embodiments, each second neural network may be trained to output an expected result corresponding to each sample in response to the inputting of a corresponding output value set, each second neural network input with output value sets from a corresponding plurality of first neural networks. In such embodiments, the pluralities of first neural networks may be unique to each second neural network, or may be the same. Likewise, the pluralities of first neural networks may receive unique aspects of the sample, the same aspects of the sample, or different combinations of aspects of the sample. Such embodiments may also involve training of a third neural network to output an expected result corresponding to each sample in response to the inputting of output corresponding to the sample from the plurality of second neural networks. Such an additional layer of the composition may improve the reduction in false positives in applicable situations.

Figure 4:
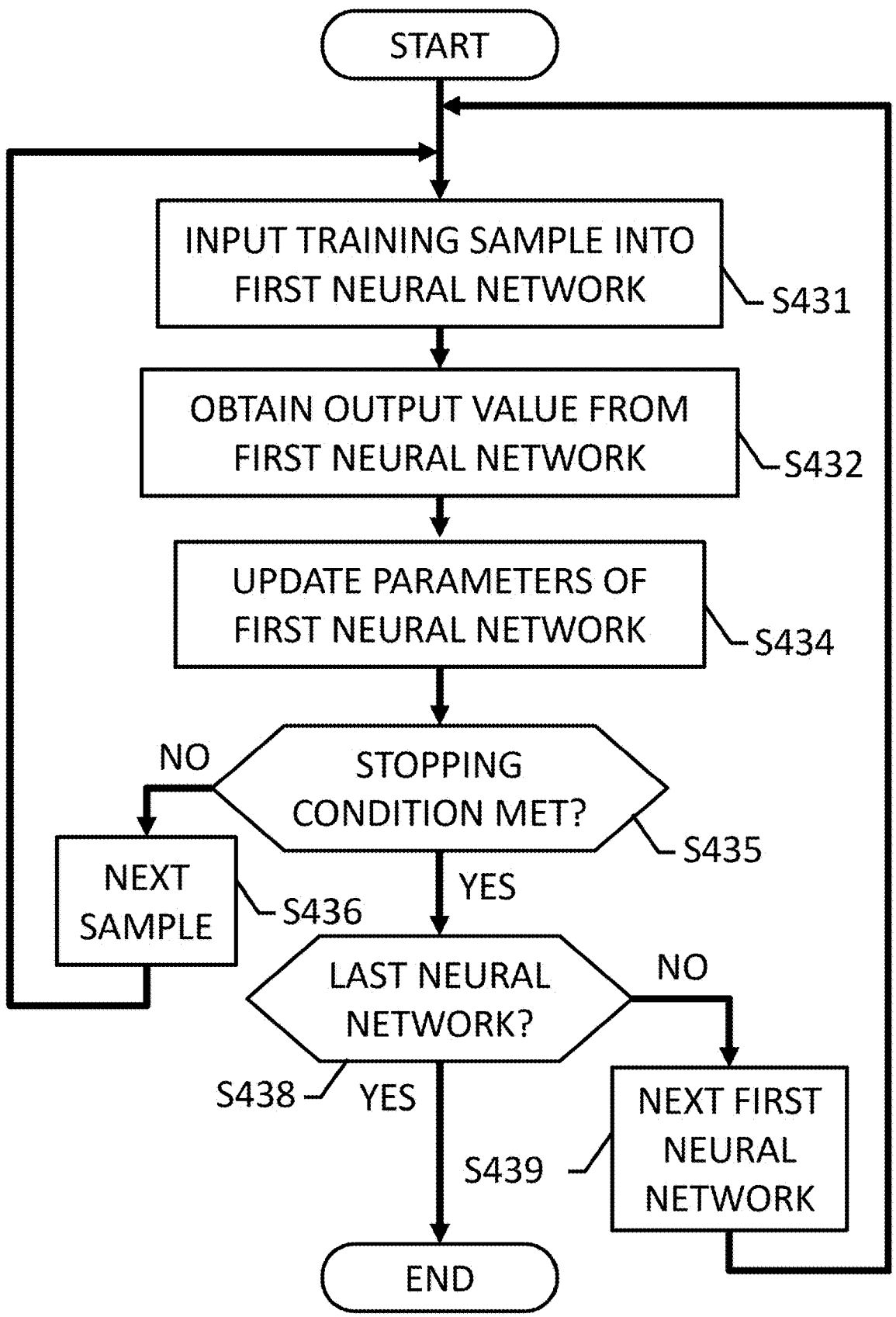
FIG. 4 shows an operational flow for training a plurality of first neural networks, according to an embodiment of the present invention.

FIG. 4 shows an operational flow for training a plurality of first neural networks, according to an embodiment of the present invention. The operational flow may provide a method of training neural networks for classification, such as plurality of first neural networks 212. The operations may be performed by an apparatus, such as apparatus 100.

At S431, an input section, such as input section 103, may input a training sample, such as sample 215, into a first neural network, such as first neural network 213A. For purposes of training, the sample is associated with a known result, which is the expected result. In some embodiments, an aspect of the sample, such as aspect 216A, is input into the first neural network.

At S432, an obtaining section, such as obtaining section 105, may obtain an output value from the first neural network. For example, the obtaining section may read the output node(s) of the first neural network once the sample has been processed by the first neural network.

At S434, a training section, such as training section 106, may update parameters of the first neural network. In some embodiments, the training of each first neural network among the plurality of first neural networks includes training each first neural network to output the expected result corresponding to each sample in response to the inputting of the corresponding sample. In other words, the parameters may be updated to improve the ability of the first neural network to correctly output the expected result.

At S435, the training section determines whether a stopping condition, such as reaching the last sample, reaching an acceptable ability, etc., has been met. If the stopping condition has not been met, then the flow proceeds to S436, in which the input section prepares and/or acquires the next sample. If the stopping condition has been met, then the flow proceeds to S438.

At S438, the training section determines whether the last first neural network has been trained. If there are more first neural networks to train, then the flow proceeds to S439, in which the input section prepares or acquires the first training sample to be input into the next first neural network, such as first neural network 213B. If the last first neural network has been trained, then the flow ends.

Figure 5:
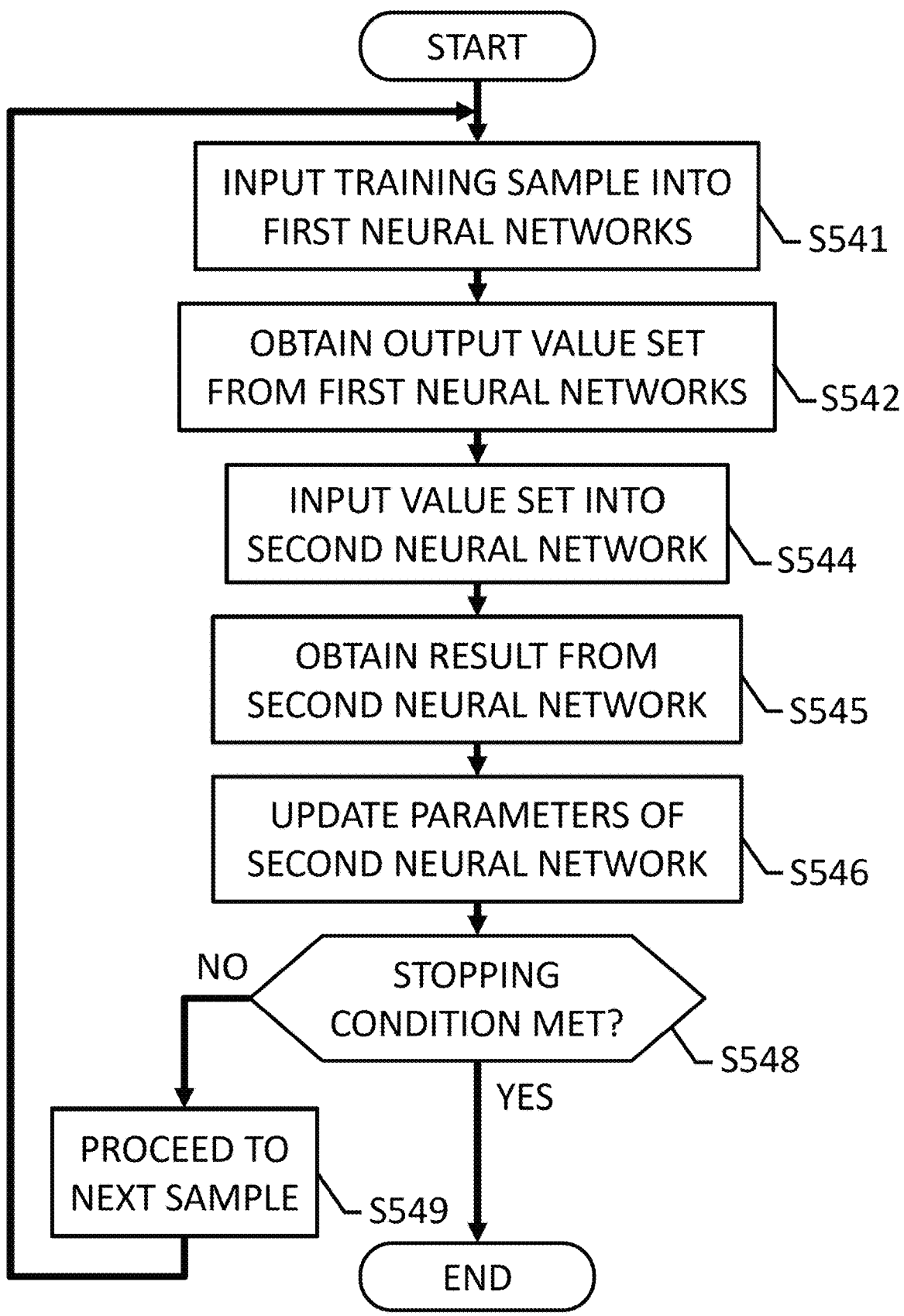
FIG. 5 shows an operational flow for training a second neural network, according to an embodiment of the present invention.

FIG. 5 shows an operational flow for training a second neural network, according to an embodiment of the present invention. The operational flow may provide a method of training a neural network for classification, such as second neural network 210. The operations may be performed by an apparatus, such as apparatus 100. While this process may be used to train the second neural network, the first neural networks are only being tested.

At S541, an input section, such as input section 103, may input a training sample, such as sample 215, into a plurality of first neural networks, such as plurality of first neural networks 212. As this flow is repeated across all of the samples of the training data set, the input section will have input the training data set into each of a plurality of first neural networks, the training data set including a plurality of samples.

At S542, an obtaining section, such as obtaining section 105, may obtain an output value from the plurality of first neural networks. As this flow is repeated across all of the samples of the training data sat, the input section will have obtained a plurality of output value sets from the plurality of first neural networks, each output value set including a plurality of output values corresponding to one of the plurality of samples, each output value being output from a corresponding first neural network in response to the inputting of one of the samples of the training data set. Operations S541 and S542 may be for purposes of testing the first neural networks. As such, the parameters of the first neural networks may not be updated during the operational flow of FIG. 5.

At S544, the input section may input an output value set into the second neural network. As this flow is repeated across all of the samples of the training data sat, the input section will have input the plurality of output value sets into the second neural network.

At S545, the obtaining section may obtain a result from the second neural network. For example, the obtaining section may read the output node(s) of the first neural network once the sample has been processed by the first neural network. As this flow is repeated across all of the samples of the training data sat, the obtaining section will have obtained all of the results from the second neural network.

At S546, a training section, such as training section 106, may update parameters of the second neural network. In some embodiments, the training of the second neural network includes training the second neural network to output an expected result corresponding to each sample in response to the inputting of a corresponding output value set. In other words, the parameters may be updated to improve the ability of the second neural network to correctly output the expected result.

At S548, the training section determines whether a stopping condition, such as reaching the last sample, reaching an acceptable ability, etc., has been met. If the stopping condition has not been met, then the flow proceeds to S549, in which the input section prepares and/or acquires the next sample. If the stopping condition has been met, then the flow ends.

Figure 6:
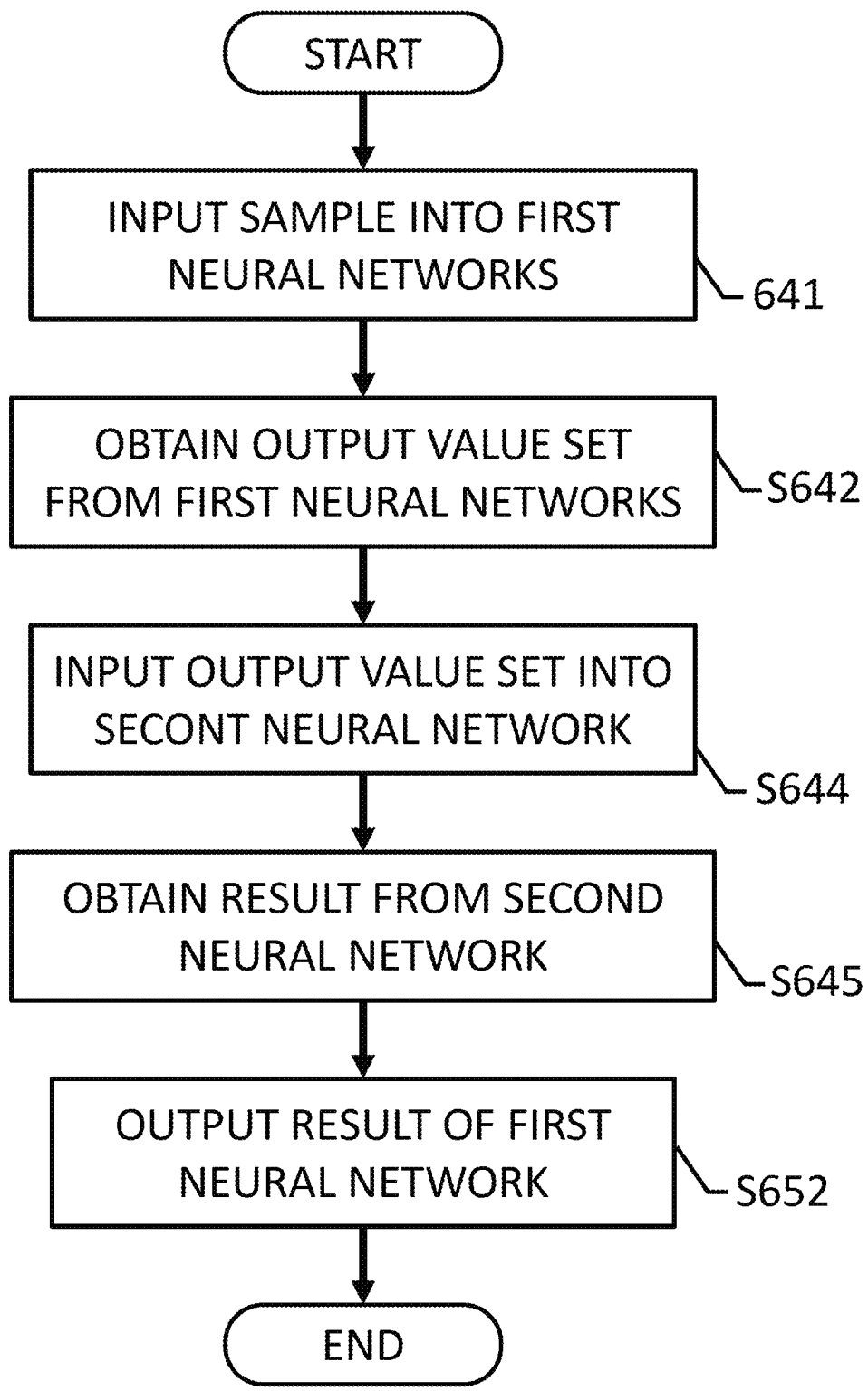
FIG. 6 shows an operational flow for neural network classification of a sample, according to an embodiment of the present invention.

FIG. 6 shows an operational flow for neural network classification of a sample, such as sample 215, according to an embodiment of the present invention. The operational flow may provide a method of training a neural network for classification, such as second neural network 210. The operational flow of FIG. 6 may be used for classification of samples having unknown results. As such, the operational flow of FIG. 6 may be effective where training of the neural networks has already been completed. The operations may be performed by an apparatus, such as apparatus 100.

At S641, an input section, such as input section 103, may input a sample, such as sample 215, into each of a plurality of first neural networks, such as plurality of neural networks 212. For example, the sample may be a 3D image volume of a patient suspected of having cancer.

At S642, an obtaining section, such as obtaining section 105, may obtain an output value set, such as output value set 218, from the plurality of first neural networks, the output value set including a plurality of output values corresponding to the sample, each output value, such as output value 219A, being output from a corresponding first neural network, such as neural network 213A, in response to the inputting of the sample. For example, the obtaining section may obtain a probability of whether a nodule exists in the sample, or aspect thereof, from each of the plurality of first neural networks.

At S644, the input section may input the output value set into the second neural network. For example, the input section may input each probability output by the plurality of first neural networks as a composition, or vector. In some embodiments, the order of the composition or vector, in terms of the corresponding first neural networks, will be the same as the order in which the second neural network was trained. In that manner, any behavioral habits that the second neural network has learned of any first neural networks will be effectively utilized.

At S645, the obtaining section may obtain a result corresponding to the sample in response to the inputting of a the output value set. For example, the obtaining section may read the output node(s) of the second neural network once the output value set has been processed by the first neural network. The output of the second neural network is also a probability of whether the sample has a nodule. This probability is intended to supersede all of the probabilities of the first neural networks, standing as the final probability, and is not intended to be another factor among the probabilities of the first neural networks.

At S652, an output section, such as output section 108, may output the result. For example, if the sample is a 3D image volume of a suspected nodule, the result may be a probability that the suspected nodule is an actual nodule. The output section may output only the probability output from the second neural network without outputting any probabilities of the first neural networks. The output section may further dismiss, discard, etc., the probabilities output from the first neural networks.

At least the foregoing embodiments may improve the reduction of false positives during classification. When compared with multi-view convolutional networks using the same training and testing samples, the foregoing embodiments performed with an error rate that was much lower than the multi-view convolutional network. More specifically, the error rate of the foregoing embodiments was 1.3% while the error rate of the multi-view convolutional networks was 9.4%.

Figure 7:
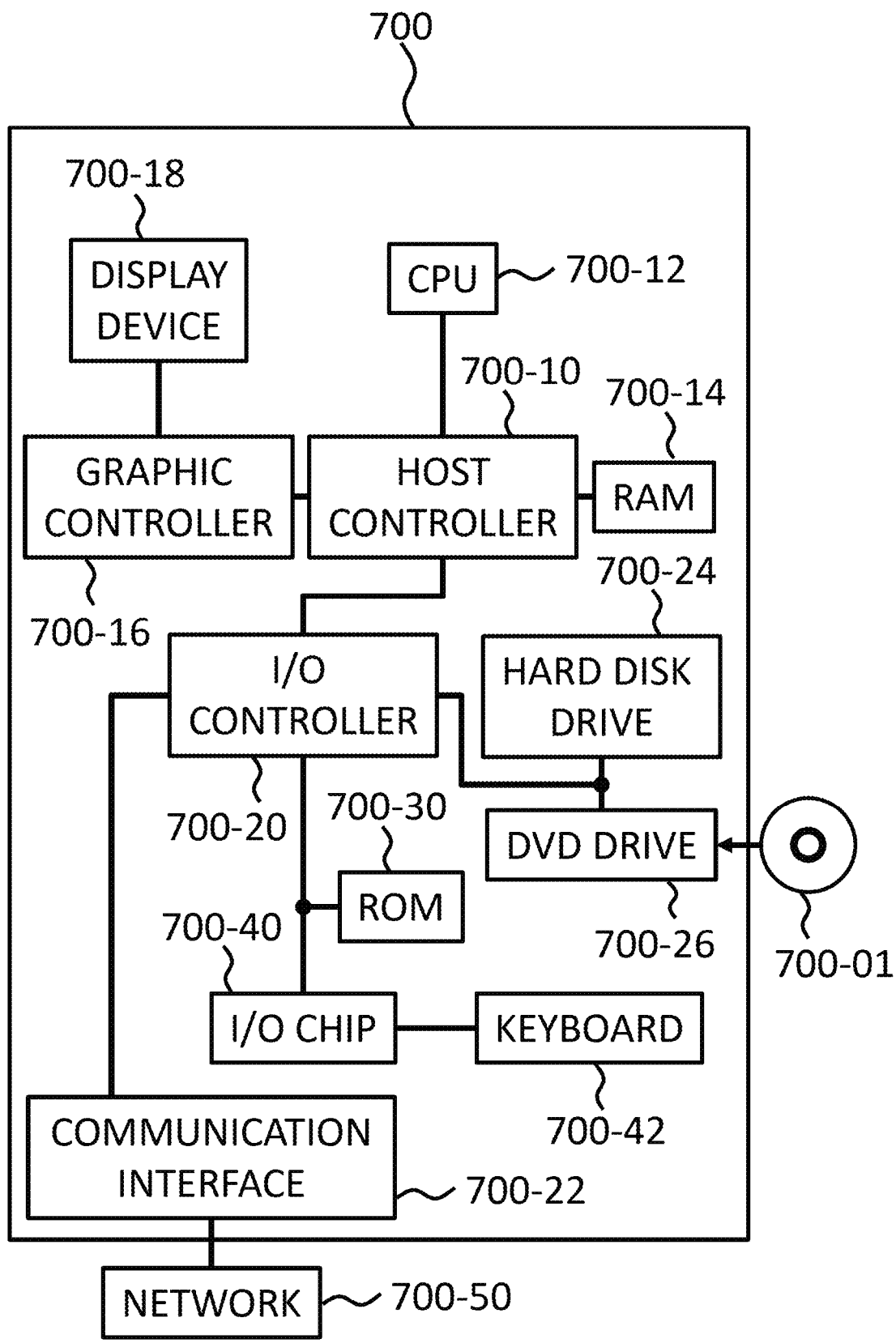
FIG. 7 shows an exemplary hardware configuration of a computer configured for cloud service utilization, according to an embodiment of the present invention.

FIG. 7 shows an exemplary hardware configuration of a computer configured to perform the foregoing operations, according to an embodiment of the present invention. A program that is installed in the computer 700 can cause the computer 700 to function as or perform operations associated with apparatuses of the embodiments of the present invention or one or more sections (including modules, components, elements, etc.) thereof, and/or cause the computer 700 to perform processes of the embodiments of the present invention or steps thereof. Such a program may be executed by the CPU 700-12 to cause the computer 700 to perform certain operations associated with some or all of the blocks of flowcharts and block diagrams described herein.

The computer 700 according to the present embodiment includes a CPU 700-12, a RAM 700-14, a graphics controller 700-16, and a display device 700-18, which are mutually connected by a host controller 700-10. The computer 700 also includes input/output units such as a communication interface 700-22, a hard disk drive 700-24, a DVD-ROM drive 700-26 and an IC card drive, which are connected to the host controller 700-10 via an input/output controller 700-20. The computer also includes legacy input/output units such as a ROM 700-30 and a keyboard 700-42, which are connected to the input/output controller 700-20 through an input/output chip 700-40.

The CPU 700-12 operates according to programs stored in the ROM 700-30 and the RAM 700-14, thereby controlling each unit. The graphics controller 700-16 obtains image data generated by the CPU 700-12 on a frame buffer or the like provided in the RAM 700-14 or in itself, and causes the image data to be displayed on the display device 700-18.

The communication interface 700-22 communicates with other electronic devices via a network 700-50. The hard disk drive 700-24 stores programs and data used by the CPU 700-12 within the computer 700. The DVD-ROM drive 700-26 reads the programs or the data from the DVD-ROM 700-01, and provides the hard disk drive 700-24 with the programs or the data via the RAM 700-14. The IC card drive reads programs and data from an IC card, and/or writes programs and data into the IC card.

The ROM 700-30 stores therein a boot program or the like executed by the computer 700 at the time of activation, and/or a program depending on the hardware of the computer 700. The input/output chip 700-40 may also connect various input/output units via a parallel port, a serial port, a keyboard port, a mouse port, and the like to the input/output controller 700-20.

A program is provided by computer readable media such as the DVD-ROM 700-01 or the IC card. The program is read from the computer readable media, installed into the hard disk drive 700-24, RAM 700-14, or ROM 700-30, which are also examples of computer readable media, and executed by the CPU 700-12. The information processing described in these programs is read into the computer 700, resulting in cooperation between a program and the above-mentioned various types of hardware resources. An apparatus or method may be constituted by realizing the operation or processing of information in accordance with the usage of the computer 700-

For example, when communication is performed between the computer 700 and an external device, the CPU 700-12 may execute a communication program loaded onto the RAM 700-14 to instruct communication processing to the communication interface 700-22, based on the processing described in the communication program. The communication interface 700-22, under control of the CPU 700-12, reads transmission data stored on a transmission buffering region provided in a recording medium such as the RAM 700-14, the hard disk drive 700-24, the DVD-ROM 700-01, or the IC card, and transmits the read transmission data to network 700-50 or writes reception data received from network 700-50 to a reception buffering region or the like provided on the recording medium.

In addition, the CPU 700-12 may cause all or a necessary portion of a file or a database to be read into the RAM 700-14, the file or the database having been stored in an external recording medium such as the hard disk drive 700-24, the DVD-ROM drive 700-26 (DVD-ROM 700-01), the IC card, etc., and perform various types of processing on the data on the RAM 700-14. The CPU 700-12 may then write back the processed data to the external recording medium.

Various types of information, such as various types of programs, data, tables, and databases, may be stored in the recording medium to undergo information processing. The CPU 700-12 may perform various types of processing on the data read from the RAM 700-14, which includes various types of operations, processing of information, condition judging, conditional branch, unconditional branch, search/replace of information, etc., as described throughout this disclosure and designated by an instruction sequence of programs, and writes the result back to the RAM 700-14. In addition, the CPU 700-12 may search for information in a file, a database, etc., in the recording medium. For example, when a plurality of entries, each having an attribute value of a first attribute is associated with an attribute value of a second attribute, are stored in the recording medium, the CPU 700-12 may search for an entry matching the condition whose attribute value of the first attribute is designated, from among the plurality of entries, and reads the attribute value of the second attribute stored in the entry, thereby obtaining the attribute value of the second attribute associated with the first attribute satisfying the predetermined condition.

The above-explained program or software modules may be stored in the computer readable media on or near the computer 700. In addition, a recording medium such as a hard disk or a RAM provided in a server system connected to a dedicated communication network or the Internet can be used as the computer readable media, thereby providing the program to the computer 700 via the network.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to individualize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

What is claimed is:

1. A method comprising:
   obtaining a plurality of output value sets from a plurality of first neural networks derived from a cascaded neural network based on a training data set comprising a plurality of samples, each output value set comprising a plurality of output values corresponding to one of the plurality of samples, each output value being output from a corresponding first neural network and comprising a probability that a disease is present in a 2D image of a plurality of 2D images input into the corresponding first neural network, wherein each sample is associated with an expected result, and wherein each sample comprises a three-dimensional (3D) image volume of a suspected disease;

obtaining, from a second neural network, a plurality of results corresponding to the plurality of samples in response to an inputting of the plurality of output value sets, each result comprising a probability that the disease is present in a 3D image volume comprised in the corresponding sample, wherein the probability that the disease is present in the 3D image volume supersedes the probability that the disease is present in the 2D image; and updating at least one parameter of the second neural network to output an expected result corresponding to each sample in response to the inputting of the corresponding output value set.

2. The method of claim 1, further comprising:
deriving the plurality of first neural networks from a cascaded Convolutional Neural Network (CNN).

3. The method of claim 1, further comprising:
training each first neural network of the plurality of first neural networks.

4. The method of claim 3, wherein the training of each first neural network among the plurality of first neural networks comprises training each first neural network to output the expected result corresponding to each sample in response to the inputting of the corresponding sample.

5. The method of claim 3, wherein each sample comprises a plurality of aspects, and each aspect corresponds to one of the plurality of first neural networks, and the training of each first neural network among the plurality of first neural networks comprises inputting the corresponding aspect among the plurality of aspects.

6. The method of claim 5, wherein the sample is a 3D image, and each aspect is an image of a plane within the 3D image.

7. The method of claim 1, wherein each first neural network among the plurality of first neural networks has a first network structure.

8. The method of claim 1, wherein at least one first neural network among the plurality of first neural networks has a first network structure, and at least one first neural network among the plurality of first neural networks has a second network structure.

9. The method of claim 1, further comprising:
recording the second neural network as a second weight value set, the second weight value set being the result of a training of the second neural network.

10. The method of claim 9, further comprising:
storing the plurality of first neural networks, each first neural network stored as a first weight value set, and the second neural network as the second weight value set in a computer-readable medium.

11. The method of claim 1, further comprising:
training a plurality of second neural networks to output an expected result corresponding to each sample in response to the inputting of a corresponding output value set, each second neural network input with output value sets from a corresponding plurality of first neural networks; and training a third neural network to output an expected result corresponding to each sample in response to the inputting of output corresponding to the sample from the plurality of second neural networks.

12. The method of claim 1, further comprising:
updating at least one parameter of the plurality of first neural networks to improve an ability to correctly output the expected result associated with each sample.

13. The method of claim 1, wherein each 2D image of the plurality of 2D images is input to a corresponding first neural network of the plurality of first neural networks.

* * * * *